(12) United States Patent
Hlatky

(10) Patent No.: US 6,384,229 B1
(45) Date of Patent: May 7, 2002

(54) TRANSITION METAL COMPLEXES CONTAINING NEUTRAL, MULTIDENTATE AZACYCLIC LIGANDS

(75) Inventor: Gregory G. Hlatky, Morrow, OH (US)

(73) Assignee: Equistar Chemicals, L.P., Houston, TX (US)

( * ) Notice: Subject to any disclaimer, the term of this patent is extended or adjusted under 35 U.S.C. 154(b) by 0 days.

(21) Appl. No.: 09/679,120

(22) Filed: Oct. 4, 2000

Related U.S. Application Data

(62) Division of application No. 09/288,093, filed on Apr. 7, 1999, now Pat. No. 6,180,552.

(51) Int. Cl.[7] .............................. C07F 19/00; C07F 7/02; C07D 249/08; B01J 31/00
(52) U.S. Cl. ..................... 548/101; 548/110; 548/250; 548/262.2; 534/15; 502/102; 502/103; 502/117; 526/127
(58) Field of Search ................................ 548/101, 110, 548/250, 255, 262.2; 534/15

(56) References Cited

U.S. PATENT DOCUMENTS

| | | | | |
|---|---|---|---|---|
| 4,554,338 A | * | 11/1985 | Wengrovius ................. | 528/18 |
| 5,064,802 A | | 11/1991 | Stevens et al. ............. | 502/155 |
| 5,504,049 A | | 4/1996 | Crowther et al. ........... | 502/117 |
| 5,539,124 A | | 7/1996 | Etherton et al. ............ | 548/402 |
| 5,554,775 A | | 9/1996 | Krishnamurti et al. ......... | 556/7 |
| 5,599,761 A | | 2/1997 | Turner ........................ | 502/152 |
| 5,637,659 A | | 6/1997 | Krishnamurti et al. ...... | 526/133 |
| 5,637,660 A | | 6/1997 | Nagy et al. ................. | 526/160 |
| 5,756,611 A | | 5/1998 | Etherton et al. ............ | 526/127 |
| 6,037,297 A | * | 3/2000 | Stibrany et al. ............ | 502/167 |
| 6,114,270 A | * | 3/2000 | Krishnamurti et al. ...... | 502/117 |
| 6,069,110 A | * | 5/2000 | Klaui et al. .................. | 502/155 |
| 6,093,673 A | * | 7/2000 | Klendworth et al. ........ | 502/103 |

FOREIGN PATENT DOCUMENTS

| | | |
|---|---|---|
| EP | 0617052 A2 | 3/1994 |
| JP | 09220476 A2 | 8/1997 |
| JP | 10338698 A2 | 12/1998 |

OTHER PUBLICATIONS

Sari Timonen et al. "Novel Single–site Catalysts Containing a Platinum Group Metal and a Macrocyclic Sulfur Ligand for Ethylene Polymerization," *Journal of Molecular Catalysis A: Chemical* vol. 111 (1996) 267–272.

Licheng Sun et al. "Binuclear Ruthenium—Manganese Complexes as Simple Artificial Models for Photosystem II in Green Plants" *J. Am Chem. Soc.* 1997, vol. 119, 6996–7004.

S. Vepachedu et al. *Acta Crystallogr., Sect. C: Cryst. Struct. Commun.* (1995), C51 (3), 423–6.

\* cited by examiner

*Primary Examiner*—Porfirio Nazario-Gonzalez
(74) *Attorney, Agent, or Firm*—Jonathan L. Schuchardt

(57) ABSTRACT

Neutral, multidentate azacyclic ligands and Group 3–10 transition metal complexes that contain them are disclosed. The ligands have the general formula: $R_a$—A—$(L)_b$ where R is hydrogen or hydrocarbyl, A is silicon, tin, germanium, or lead, each L is a pyrazolyl, triazolyl, or tetraazolyl group, a=0 to 2, b=2 to 4, and a+b=4. When used with common activators, the transition metal complexes provide excellent single-site catalysts for olefin polymerization.

5 Claims, No Drawings

TRANSITION METAL COMPLEXES CONTAINING NEUTRAL, MULTIDENTATE AZACYCLIC LIGANDS

This is a division of application Ser. No. 09/288,093, filed Apr. 7, 1999, now U.S. Pat. No. 6,180,552.

FIELD OF THE INVENTION

The invention relates to neutral pyrazolyl, triazolyl, and tetraazolyl-containing ligands ("azacyclic" ligands) and transition metal complexes that contain them. The complexes are valuable procatalysts for organic reactions, particularly for olefin polymerizations.

BACKGROUND OF THE INVENTION

The chemical industry uses a wide variety of transition metal complexes as catalysts for organic reactions. Polyolefin manufacture is a good example. While conventional Ziegler-Natta catalysts continue to dominate the industry, highly active metallocene or single-site catalysts that give new polymers with narrow molecular weight distributions, low densities, and good comonomer incorporation are emerging.

Transition metal complexes used to polymerize olefins are normally non-zero-valent metals (e.g., $Ti^{4+}$, $Zr^{4+}$, $Sc^{3+}$) surrounded by anionic ligands (e.g., chloride, alkyl, cyclopentadienyl) that satisfy the valency of the metal and often improve the solubility of the catalyst in the reaction medium. The anionic ligands can dramatically impact catalyst activity and polymer properties.

Neutral, multidentate ligands have been used only sparingly in preparing the transition metal complexes useful as precursors for metallocene or single-site polyolefin catalysts. For example, 1,4,7-trimethyl-1,4,7-triazacyclononane (tmtacn) has been used to prepare (tmtacn)$MCl_3$ complexes of scandium, chromium, and rhodium (see, for example, Wang et al., *J. Am. Chem. Soc.* 119 (1993) 6999); derivatives of these complexes catalyze olefin polymerizations. Another example is 1,4,7-trithiacyclononane (ttcn), from which (ttcn)$RhCl_3$ has been prepared (S. Timonen et al., *J. Mol. Catal. A.*, 111 (1996) 267). Because of their complexity, high cost, and synthetic challenge, such ligands have not been widely pursued. While more accessible neutral ligands (such as 1,2-bis(diphenylphosphino)ethane) exist, these have not generally provided significant advantages for metallocene and single-site catalysts.

A potentially viable route to neutral, multidentate ligands reacts three equivalents of pyrazole with chloroform in the presence of a base to give a tris(pyrazolyl)methane. This method is economically attractive because a variety of pyrazoles can be made by reacting acetylacetones with hydrazine. Unfortunately, carbene formation complicates the product mixture and reduces the yield of the desired tris(pyrazolyl) compound.

Anionic tris(pyrazolyl)borate ligands are known. U.S. Pat. No. 5,504,049, for example, reacts $VOCl_3$ with potassium tris(pyrazolyl)borate to make a complex that polymerizes ethylene in the presence of an activator such as MAO. In addition, one tris(pyrazolyl)silane compound is known: S. Vepachedu et al. (*Acta Cryst. C*51 (1995) 423)) reported the crystal structure of tris(3,5-dimethylpyrazolyl)methylsilane.

In sum, new neutral, multidentate ligands are needed. Particularly valuable ligands would be easy to synthesize from readily available starting materials. Preferably, the ligands could be made in high yields without complicating side reactions such as carbene formation. Ideally, the ligands would be valuable for making new transition metal complexes useful as procatalysts for olefin polymerization.

SUMMARY OF THE INVENTION

The invention is a new class of neutral, multidentate ligands. The ligands have the general formula: $R_a$—A—$(L)_b$ where R is hydrogen or $C_1$–$C_{30}$ alkyl, aryl, or aralkyl, A is silicon, tin, germanium, or lead, each L is independently a substituted or unsubstituted pyrazolyl, triazolyl, or tetraazolyl group, a=0 to 2, b=2 to 4, and a+b=4, with the proviso that when R=methyl, A is silicon, and a=1, then L is not a 3,5-dimethylpyrazolyl group.

The invention includes transition metal complexes which comprise a Group 3 to 10 transition or lanthanide metal (M), one or more anionic or neutral ligands in an amount that satisfies the valency of M, and the neutral, multidentate ligand described above. The invention also includes catalysts for olefin polymerization; these comprise the transition metal complexes and an activator such as MAO or a borate salt. Finally, the invention includes an olefin polymerization process that uses the catalysts.

I surprisingly found that neutral, multidentate ligands based on Group 14 elements (silicon, tin, germanium, or lead) and pyrazolyl, triazolyl, or tetraazolyl groups are easy to synthesize and purify. Moreover, the ligands readily react with Group 3 to 10 transition and lanthanide metals to give complexes that are potentially valuable for a wide range of organic transformations, including olefin metathesis, isomerization, oligomerization, and the like. In particular, the complexes react with common activators such as aluminoxanes or borate salts to provide excellent single-site catalysts for olefin polymerization.

DETAILED DESCRIPTION OF THE INVENTION

The neutral, multidentate azacyclic ligands of the invention have the general formula $R_a$—A—$(L)_b$. In the formula, A is a Group 14 element, excluding carbon. In other words, A can be silicon, germanium, tin, or lead. Silicon is preferred. R is hydrogen or a $C_1$–$C_{30}$ alkyl, aryl, or aralkyl group. Preferably, R is hydrogen or a $C_1$–$C_5$ alkyl group. Each L is independently a pyrazolyl, triazolyl, or tetraazolyl group; a=0 to 2, preferably 1 to 2; b=2 to 4, preferably 2 to 3; and a+b=4.

By "pyrazolyl," we mean a group with the structure:

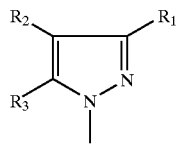

in which any of the three ring carbons is unsubstituted (i.e., has one hydrogen) or is substituted with $R_1$, $R_2$, and/or $R_3$, each of which may be independently a hydrocarbyl, halide, alkoxide, dialkylamino, nitro, or similar group. Two adjacent hydrocarbyl groups may be joined to form a cyclic structure, as in indazole or tetrahydroindazole. The pyrazolyl groups are sigma-bonded to the silicon, tin, germanium, or lead atom through the 1-nitrogen. Unsubstituted and hydrocarbyl-substituted pyrazolyl groups are preferred.

Similarly, triazolyl ligands have the following structures:

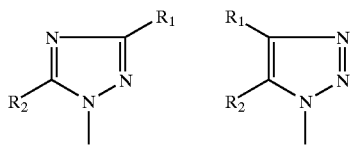

in which $R_1$ and $R_2$ are defined as above.

A tetraazolyl ligand has the following structure:

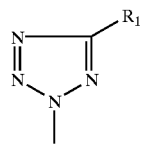

in which $R_1$ is defined as above.

Suitable neutral, multidentate ligands include, for example, bis(pyrazolyl)dimethylsilane, bis(pyrazolyl)methylphenylsilane, bis(pyrazolyl)diphenylsilane, bis(pyrazolyl)bis(dimethylamino)silane, bis(pyrazolyl)silacyclobutane, bis(pyrazolyl)silacyclopentane, bis(3,5-dimethylpyrazolyl)dimethylsilane, bis(indazole)dimethylsilane, bis(4-chloropyrazolyl)dimethylsilane, bis(4-methylpyrazolyl)dimethylsilane, bis(3,5-trifluoromethylpyrazolyl)dimethylsilane, tris(pyrazolyl)methylsilane, bis(pyrazolyl)methylsilane, tris(3-methylpyrazolyl)methylsilane, tetrakis(pyrazolyl)silane, bis(triazolyl)dimethylsilane, bis(benzotriazolyl)dimethylsilane, tris(benzotriazolyl)methylsilane, bis(tetraazolyl)dimethylsilane, tris(tetraazolyl)methylsilane, tris(pyrazolyl)methyltin, tris(3,5-dimethylpyrazolyl)germane, tris(pyrazolyl)methylgermane, tetra(pyrazolyl)lead, tetra(3,5-dichloropyrazolyl)silane, and the like, and mixtures thereof. Particularly preferred are bis and tris (pyrazolyl)alkylsilanes and bis and tris(3,5-disubstituted pyrazolyl)alkylsilanes.

The neutral, multidentate ligands are easy to prepare. The azacycles (e.g., pyrazole, 3,5-dimethylpyrazole, benzotriazole, tetrazole, and the like) are often commercially available. In one convenient preparation, the azacycle is deprotonated by reacting it with a strong base such as n-butyllithium in an inert solvent (e.g., ether). Evaporation of solvent gives the alkali metal salt. Two to four equivalents of this salt are then reacted with a Group 14 compound, preferably one having an equivalent number of good leaving groups (e.g., three moles of azacycle salt and one mole of methyltrichlorosilane) to produce the neutral, multidentate ligand. The workup usually consists of dissolving the reaction products in a solvent (hydrocarbon or halogenated hydrocarbon, e.g.), filtering to remove alkali metal salts, and recrystallizing the ligand. Examples 1–4 below illustrate how to prepare the neutral ligands of the invention.

The invention includes transition metal complexes prepared with the neutral, multidentate ligands. The transition metal complexes comprise, in addition to the neutral, multidentate ligand, a Group 3 to Group 10 transition or lanthanide metal, M, and one or more anionic or neutral ligands in an amount that satisfies the valency of M.

Group 3–10 metals comprise Sc, Ti, V, Cr, Mn, Fe, Co, Ni, and elements directly below these elements in the Periodic Table. Suitable lanthanide metals include La, Ce, Pr, Eu, Yb, and the like. Preferred are Group 3–6 transition and lanthanide metals; most preferred are Group 4 transition metals.

Anionic or neutral ligands make up the balance of the transition metal complex. Examples include unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, boraaryl groups, or the like, and combinations of these. Examples of neutral ligands are carbonyl, $\eta^6$-aryl, $\eta^4$-butadiene, $\eta^4$-cyclobutadiene, $\eta^4$-cyclooctatetraene, tertiary phosphine, and the like. Other examples of suitable anionic or neutral ligands appear in U.S. Pat. Nos. 5,756,611, 5,637,659, 5,637,660, 5,554,775, and 5,539,124, the teachings of which are incorporated herein by reference.

Any convenient source of transition metal can be used. For example, the complexes can be made from transition metal halides, alkyls, alkoxides, acetates, amides, or the like. A particularly convenient source of the transition metal is the transition metal halide. For example, one can use vanadium(III)chloride-tetrahydrofuran complex ($VCl_3$(THF)$_3$), titanium (III)chloride THF complex, chromium (III)chloride-THF complex, cobalt(II) chloride, nickel(II) bromide, platinum(II)chloride, palladium(II)chloride, lanthanum(III) chloride, titanium(III)acetate, or the like. Complexes can also be prepared from salts with labile groups, such as tetrakis(acetonitrile)palladium(II) bis (tetrafluoroborate).

The transition metal complexes are easy to make. Usually, the transition metal source (halide, e.g.) is dissolved or suspended in an organic solvent and the neutral, multidentate ligand is carefully added. Refluxing is used if needed to complete the reaction. Insoluble by-products, if any, can be removed by filtration, solvents are evaporated, and the transition metal complex is isolated, washed, and dried. The resulting complex can generally be used without further purification.

Binuclear complexes (containing more than one metal center) can be prepared by the reaction of two equivalents of a suitable metal precursor with a tetrakis(azacyclic)silane. Thus, reacting two equivalents of $NiCl_2$ with $(C_3H_3N_2)_4Si$ (i.e., (Pz)$_4$Si) should afford the binuclear complex $Cl_2Ni(Pz)_2Si(Pz)_2NiCl_2$. Similarly, dendrimeric multiarmed ligands such as [(Pz)$_3$SiCH$_2$CH$_2$]$_4$Si (prepared from 12 equivalents of Li(Pz) with [Cl$_3$SiCH$_2$CH$_2$]$_4$Si) should give polynuclear metal complexes.

Transition metal complexes of the invention are expected to be valuable catalysts, catalyst precursors, or reagents for a variety of organic reactions, including, for example, olefin metathesis, isomerization, and polymerization reactions.

The invention includes catalysts which comprise the transition metal complexes described above and an activator. Generally, the activator converts the complex to a cationically active species. The catalysts are especially valuable for polymerizing olefins, such as ethylene, propylene, and/or other $\alpha$-olefins such as 1-butene or 1-hexene.

Suitable activators are well known in the art. Examples include alumoxanes (methyl alumoxane (MAO), PMAO, ethyl alumoxane, diisobutyl alumoxane), alkylaluminum compounds (triethylaluminum, diethylaluminum chloride, trimethylaluminum), and the like. Such activators are generally used in an amount within the range of about 0.01 to about 100,000, preferably from about 1 to about 10,000, moles per mole of transition metal complex.

Suitable activators include acid salts that contain non-nucleophilic anions. These compounds generally consist of bulky ligands attached to boron or aluminum. Examples include lithium tetrakis(pentafluorophenyl) borate, lithium tetrakis(pentafluorophenyl)aluminate, anilinium tetrakis (pentafluorophenyl)borate, and the like. These activators are generally used in an amount within the range of about 0.01 to about 1000, preferably from about 1 to about 10, moles per mole of transition metal complex.

Suitable activators also include trialkyl or triarylboron compounds such as tris(pentafluorophenyl)boron, tris(pentabromophenyl)boron, and the like. Other suitable activators are described, for example, in U.S. Pat. Nos. 5,756,611, 5,064,802, and 5,599,761, the teachings of which are incorporated herein by reference.

The catalysts are optionally used with an inorganic solid or organic polymer support. Suitable supports include silica, alumina, silica-aluminas, magnesia, titania, clays, zeolites, or the like. The supports can be pretreated thermally or chemically to improve catalyst productivity or product properties. The catalysts can be deposited on the support in any desired manner. For instance, the catalyst can be dissolved in a solvent, combined with a support, and stripped. Alternatively, an incipient-wetness technique can be used. Moreover, the support can simply be introduced into the reactor separately from the catalyst. The ligand can also be chemically tethered to the support through a suitable linking group.

The invention includes an olefin polymerization process. The process comprises polymerizing an olefin in the presence of a catalyst of the invention according to methods that are well known in the art. Suitable techniques include gas, high-pressure liquid, slurry, solution, or suspension-phase processes and combinations of these. Suitable olefins include ethylene, propylene, butenes, pentenes, hexenes, octenes, styrenes, 1,3-butadiene, norbornene, and the like. Preferred olefins are ethylene, propylene, and α-olefins such as 1-butene, 1-hexene, and 1-octene. Examples 11 and 12 below illustrate a lab-scale process of the invention for making polyethylene.

The following examples merely illustrate the invention. Those skilled in the art will recognize many variations that are within the spirit of the invention and scope of the claims.

EXAMPLES 1–4

Ligand Preparation

EXAMPLE 1

Preparation of Bis(pyrazolyl)dimethylsilane

Pyrazole (6.81 g) is dissolved in ether (125 mL), and n-butyllithium (40 mL of a 2.5 M solution in hexane) is added. After 0.5 h, the solvent is evaporated, and pentane is added. The white solids (7.30 g) are filtered off and dried.

The solids are dissolved in ether (100 mL), and dichlorodimethylsilane (6.36 g) in ether (10 mL) is added dropwise. The cloudy suspension is stirred overnight and filtered. The filtrate is evaporated, and the residue is dissolved in warm pentane and filtered. Cooling of the filtrate to −30° C. precipitates white solids (7.26 g). $^1$H NMR (toluene-d$_8$): 0.64 (s, CH$_3$—Si), 6.09 (t), 7.28 (d), 7.70 (d).

EXAMPLE 2

Preparation of Bis(3,5-dimethylpyrazolyi) dimethylsilane 3,5-Dimethylpyrazole (9.61 g) is dissolved in ether (175 mL), and n-butyllithium (10 mL of a 10 M solution in hexane) is added. After 1.5 h, the mixture is evaporated, and pentane is added. Cooling to −30° C. precipitates white solids (8.53 g), which are filtered off and dried.

The solids are dissolved in ether (100 mL), and dichlorodimethylsilane (5.40 g) in ether (10 mL) is added dropwise. A white solid precipitates. The mixture is refluxed for 1.5 h, and is then cooled to room temperature and filtered. The filtrate is evaporated, and the resulting white crystals are dissolved in pentane and filtered. Cooling of the filtrate to −30° C. precipitates white crystals (5.43 g). $^1$H NMR (toluene-d$_8$): 0.82 (s, CH$_3$—Si), 1.79 (s), 2.20 (s), 5.69 (s).

EXAMPLE 3

Preparation of Tris(pyrazolyl)methylsilane

Pyrazole (6.81 g) is dissolved in ether (125 mL), and n-butyllithium (40 mL of a 2.5 M solution in hexane) is added. After 0.5 h, the solvent is evaporated, and pentane is added. The white solids (7.20 g) are filtered off and dried.

The solids are dissolved in ether (150 mL), and trichloromethylsilane (4.85 g) in ether (15 mL) is added dropwise. The mixture is stirred overnight and filtered. The filtrate is evaporated, and the residue is dissolved in warm pentane and filtered. Cooling of the filtrate to −30° C. precipitates white crystals (5.13 g). $^1$H NMR (toluene-d$_8$): 1.04 (s, CH$_3$—Si), 5.89 (t), 7.21 (s), 7.52 (s).

EXAMPLE 4

Preparation of Tris(3,5-dimethylpyrazolyl) methylsilane 3,5-Dimethylpyrazole (19.2 g) is dissolved in ether (150 mL), and n-butyllithium (20 mL of a 10 M solution in hexane) is added. After 0.5 h, the solvent is evaporated, and the solids are collected with hexane and cooled to −30° C. Yield: (14.7 g).

The solids are dissolved in ether (125 mL), and trichloromethylsilane (7.17 g) is added dropwise. The mixture is refluxed for 1 h, cooled, and filtered. The filtrate is evaporated, and the residue is dissolved in pentane (200 mL) and filtered. Cooling of the filtrate to −30° C. precipitates white crystals (9.84 g). $^1$H NMR (toluene-d$_8$): 1.58 (s, 3-CH$_3$ and CH$_3$—Si), 2.19 (s), 5.69 (s).

EXAMPLES 5–10

Preparation of Transition Metal Complexes

EXAMPLE 5

Preparation of MeSi(Me$_2$Pz)$_3$VCl$_3$

Vanadium (III) chloride-tetrahydrofuran complex (VCl$_3$ (THF)$_3$, 1.86 g) is dissolved in 2:1 CH$_2$Cl$_2$/THF solution (40 mL). The product of Example 4 (1.64 g) dissolved in CH$_2$Cl$_2$ (15 mL) is added slowly. After 15 min., an olive green precipitate forms. The mixture is stirred overnight and filtered. The solids are washed with CH$_2$Cl$_2$ and pentane and are dried. Yield: 1.59 g.

EXAMPLE 6

Preparation of MeSi(Me$_2$Pz)$_3$CrCl$_3$

Chromium (III) chloride-tetrahydrofuran complex (CrCl$_3$ (THF)$_3$, 1.87 g) is suspended in CH$_2$Cl$_2$ (30 mL). The product of Example 4 (1.62 g) dissolved in CH$_2$Cl$_2$ (15 mL) is added slowly. The purple suspension turns clear and green. After 30 min., the solution is filtered, and the filtrate is evaporated. The solids are washed with pentane and dried. Yield: 2.19 g.

EXAMPLE 7

Preparation of MeSi(Me$_2$Pz)$_3$TiCl$_3$

Titanium (III) chloride-tetrahydrofuran complex (TiCl$_3$ (THF)$_3$, 2.57 g) is dissolved in a 3:1 CH$_2$Cl$_2$/THF solution (40 mL). The product of Example 4 (1.70 g) dissolved in $CH_2Cl_2$ (40 mL) is added. After 1 h, the solvent is evaporated, and the solids are collected with pentane. Yield: 2.49 g.

EXAMPLE 8

Preparation of $MeSi(Pz)_3TiCl_3$

Titanium (III) chloride-tetrahydrofuran complex ($TiCl_3$ $(THF)_3$, 1.85 g) is dissolved in $CH_2Cl_2$ (15 mL). The product of Example 3 (1.22 g) dissolved in $CH_2Cl_2$ (30 mL) is added. An aquamarine precipitate forms almost immediately. After 45 min., the solids are filtered off, washed with $CH_2Cl_2$ and pentane, and dried. Yield: 2.00 g.

EXAMPLE 9

Preparation of $Me_2Si(Me_2Pz)_2CoCl_2$

Cobalt (II) chloride (1.00 g) and the product of Example 2 (1.54 g) are refluxed in THF (50 mL) for 1 h. The solvent is evaporated, and the solids are collected with pentane. Yield: 2.10 g.

EXAMPLE 10

Preparation of $Me_2Si(Me_2Pz)_2NiBr_2$

Nickel (II) bromide (1.09 g) is suspended in THF (30 mL). The product of Example 2 (1.24 g) is added and the brown solid turns blue. The mixture is refluxed for 1.5 h and is filtered. The filtrate is evaporated, and the blue solids are collected with pentane, filtered, and dried. Yield: 0.29 g.

EXAMPLES 11–12

Polyethylene Preparation

EXAMPLE 11

Polymerization with $MeSi(Me_2Pz)_3CrCl_3$

Methyl alumoxane (10 mL of 10 wt. % MAO in toluene) is added to the product of Example 6 (10 mg). The mixture is injected into a 1.7 L stainless-steel autoclave containing dry, deoxygenated toluene (850 mL). The autoclave is heated to 80° C. and is pressurized with ethylene (150 psi). After 1 h, the autoclave is cooled, and the contents are evaporated under a nitrogen stream. Yield of polyethylene: 12.1 g.

EXAMPLE 12

Polymerization with $MeSi(Me_2Pz)_3VCl_3$

Methyl alumoxane (10 mL of 10 wt. % MAO in toluene) is added to the product of Example 5 (8 mg). The mixture is polymerized under the conditions of Example 11. Yield of polyethylene: 2.1 g.

The preceding examples are meant only as illustrations; the following claims define the scope of the invention.

I claim:

1. A transition or lanthanide metal complex which comprises:
   (a) a Group 3 to 10 transition or lanthanide metal, M;
   (b) one or more anionic or neutral ligands in an amount that satisfies the valency of M; and
   (c) a neutral, multidentate ligand of the formula:

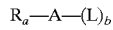

wherein R is hydrogen or a $C_1$–$C_{30}$ alkyl, aryl, or aralkyl, A is silicon, tin, germanium, or lead, each L is independently a substituted or unsubstituted triazolyl or tetraazolyl group, a=0 to 2, b=2 to 4, and a+b=4.

2. The transition or lanthanide metal complex of claim 1 which comprises a Group 3 to 6 transition or lanthanide metal.

3. The transition or lanthanide metal complex of claim 1 wherein A is silicon.

4. A transition or lanthanide metal complex which comprises:
   (a) a Group 3 to 10 transition or lanthanide metal, M, in a 3+ oxidation state;
   (b) one or more anionic or neutral ligands in an amount that satisfies the valency of M; and
   (c) a neutral, multidentate ligand of the formula:

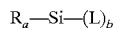

wherein R is hydrogen or a $C_1$–$C_{30}$ alkyl, aryl, or aralkyl, each L is independently a substituted or unsubstituted pyrazolyl group, a=0 to 2, b=2 to 4, and a+b=4.

5. The transition or lanthanide metal complex of claim 4 wherein M is a Group 3 to 6 transition or lanthanide metal.

* * * * *